United States Patent [19]

Frey et al.

[11] Patent Number: 5,295,829
[45] Date of Patent: Mar. 22, 1994

[54] WATER SUPPLY DEVICE FOR DENTAL WORK STATIONS

[75] Inventors: Hans-Peter Frey, Mannheim; Hans-Michael Kratochwilla, Lorsch, both of Fed. Rep. of Germany

[73] Assignee: Siemens Aktiengesellschaft, Munich, Fed. Rep. of Germany

[21] Appl. No.: 918,055

[22] Filed: Jul. 24, 1992

[30] Foreign Application Priority Data

Jul. 24, 1991 [EP] European Pat. Off. ......... 91112441

[51] Int. Cl.[5] ............... A61C 1/10; A61C 1/12; A61C 1/02; A61G 17/02
[52] U.S. Cl. .................. 433/82; 433/80; 433/98
[58] Field of Search ................ 433/80, 82, 84, 88, 433/98

[56] References Cited

U.S. PATENT DOCUMENTS

| | | |
|---|---|---|
| 4,276,023 | 6/1981 | Phillips et al. ............... 433/85 |
| 4,302,185 | 11/1981 | Hall ............................... 433/27 |
| 4,545,956 | 10/1985 | Ciszewski et al. . | |
| 4,699,589 | 10/1987 | Friedman et al. ........... 433/80 |
| 5,044,952 | 9/1991 | Castellini .................... 433/84 |
| 5,074,787 | 12/1991 | Tsukada ....................... 433/98 |
| 5,158,454 | 10/1992 | Viebahn et al. ............. 433/82 |

FOREIGN PATENT DOCUMENTS

| | | |
|---|---|---|
| 0111249 | 2/1986 | European Pat. Off. . |
| 2032640 | 1/1972 | Fed. Rep. of Germany . |
| 3901320 | 6/1990 | Fed. Rep. of Germany . |

*Primary Examiner*—John J. Wilson
*Assistant Examiner*—Cindy A. Cherichetti
*Attorney, Agent, or Firm*—Hill, Steadman & Simpson

[57] ABSTRACT

A water supply device for dental apparatuses which is provided with an arrangement to prevent backflow of contaminated water from any one of the dental apparatuses into the fresh water supply is characterized by providing a separate container for receiving water from the water system and a pump for pumping water from the container through lines to each of the discharge locations for the dental apparatus. In one embodiment, the pump is driven by an electrical motor and in another embodiment the pump is formed by two air-actuated piston pumps that work asynchronously. The arrangement can include a second container for disinfectant, which is discharged into the first container as fluid is added to the first container.

18 Claims, 4 Drawing Sheets

WATER SUPPLY DEVICE FOR DENTAL WORK STATIONS

BACKGROUND OF THE INVENTION

The present invention is directed to a water supply arrangement for a dental work station that contains a plurality of equipment having withdrawal locations to which water is supplied from a drinking water main, wherein at least one of the withdrawal locations cannot be arranged at a safe distance with reference to a drain allocated to the withdrawal location, as required according to technical rules for protecting drinking water.

The technical rules for drinking water supply installation prescribes specific safety measures in the water supply installation for protecting the drinking water. Among the things to be avoided is a backflow of any water, which is contaminated at a withdrawal location, into the public drinking water network and, thus, is subsequently supplied to another user as drinking water. The reasons and prescribed safety measures for preventing backflow are defined in detail in DIN 1988, Part 4, which is dated December 1988.

A dental work station containing equipment wherein the safe distance between a withdrawal location and a drain required in the above-mentioned DIN Standards can be observed, for example, in the rotary rinsing of the expectoration means or at the intake for a filling means for an oral rinsing glass. In other equipment, such as drills or spray handpieces, this safe distance cannot be observed, since a fixed allocation between a withdrawal location and the exit location of the water and a drain is not established.

SUMMARY OF THE INVENTION

The present invention is direct to the object of providing a water supply means for a dental work station that assures that a backflow of contaminated water and, thus, a deterioration of the drinking water quality can be avoided, even at those withdrawal locations at which the safety measures required for protecting the drinking water cannot be realized, namely in the very offering of the water supply for the individual equipment.

To accomplish these goals, the present invention is directed to an improvement in a water supply device for a dental work station that contains a plurality of equipment comprising water exits or, respectively, withdrawal locations, and to which water is supplied from a drinking water line network whereby at least one of the withdrawal locations cannot be arranged at a safe distance with respect to a drain allocated to the withdrawal location, which distance is required according to the technical rules for protecting drinking water. The improvements are providing isolation means in a line leading at least to said withdrawal location, which separates drinking water feed within the framework of the prescribed safety measures and an actuator or pump is provided in the line section following the separating means, said actuator or pump increasing the water pressure in this line section, which is supplied to a valve required at the withdrawal location. The proposed separation of the drinking water feed that is preferably fashioned as a free discharge into a container assures a reliable protection for the drinking water within the framework of the initially-cited rules for drinking water systems, namely in combination with the actuator or pump provides following therefrom in the flow direction.

The isolation or separating means that are provided preferably comprise a first container into which water from the drinking water supply is introduced with a free discharge. The advantageous development of the invention provides a second container from which a disinfectant liquid can be conducted into the first container via a second free discharge. The disinfectant liquid can, thus, be added to the drinking water while observing the above-mentioned safety rules.

Although it is possible to provide any suitable pump or actuator which is driven by air to pump a fluid for increasing the water pressure in the line section leading to the withdrawal location that is suitable for providing application with respect to conveying pressure and conveying capacity, it proves especially advantageous to provide an electromotively driven positive displacement pump that is controlled via pneumatic operating switches. Alternatively thereto, two pneumatically chargeable, asynchronously operated hydraulic pumps can also be provided.

Other advantages and features of the invention will be readily apparent from the following description of the preferred embodiments, the drawings and claims.

DESCRIPTION OF THE PREFERRED EMBODIMENTS

Figure 1:
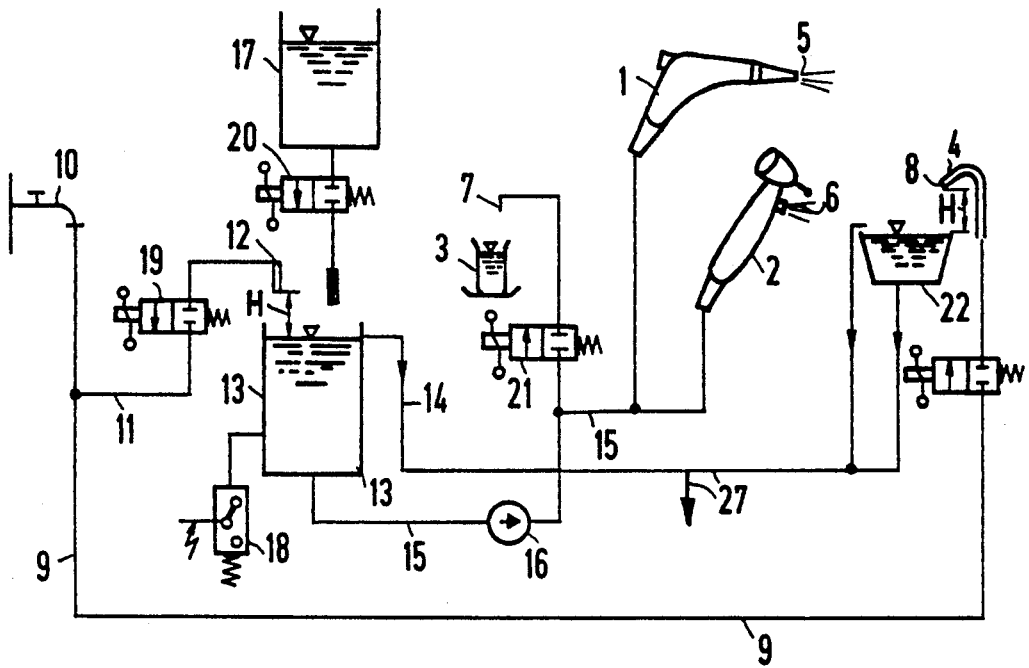
FIG. 1 is a schematic diagram of a hydraulic supply of a dental work station in accordance with the present invention.

The principles of the present invention are particularly useful in a hydraulic supply plan illustrated in FIG. 1. The work station recited herein as an example contains four equipment that use water. These include a dental spray 1, a drill handpiece 2, a filling means 3 for an oral rinse glass, as well as a rotary expectorant basin rinser 4. The water discharge or withdrawal location for the handpiece 1 is indicated at 5, for the handpiece 2 is indicated at 6 for the filling means 3 is a nozzle 7 and for the basin rinser 4 is a nozzle 8. While the basin discharge location or nozzle 8 of the basin rinser 4 has a fixed allocation or distance H to a basin 22 of that device that allows a safe distance from the highest possible water level, as defined in the above-mentioned standard DIN 1988, which device is defined by the overflow (not referenced in detail), the safety measures are not possible in the case of the equipment 1-3. Consequently, only the rotary expectorant basin rinser 4 is directly connected to the drinking supply line network 10 via a line 9. By contrast thereto, the equipment 1-3 are not directly connected to the drinking water supply network. On the contrary, the water conduit leading to these users comprises a point of separation in that the line section 11 connected to the drinking supply network 10 ends in a filler neck or discharge 12 that forms a free discharge for a container 13. This free discharge 12 has a safe distance H above the highest possible water level for the container 13, as prescribed by the standard DIN 1988, and this highest possible water level is defined by an overflow 14 which is connected to a central drain 27.

The container 13 has the job of preparing the water for removal and, as warranted, accepts a disinfectant which can be received from an additional container 17 with a free discharge.

A conveying pump 16 serving as an air-driven actuator for moving liquids is situated in a line section 15 that leads from the container 13 to the equipment 1-3. This conveying pump 16 conveys water from the container to the withdrawal locations with the required pressure and the necessary volume. The filling level of the container 13 is controlled by a level switch 18 that actuates a solenoid valve 19 when a defined container level is downwardly passed or transgressed, as a result of which fresh water from the line network 10 is conducted into the container via the free discharge 12. The filling level can be determined either by a timer element or by a second level indicator switch. The control of the solenoid valve 20 for supplying disinfectant can, preferably, occur simultaneously with the supply of the fresh water. The setting of the quantity of the disinfectant per time unit can occur with the assistance of a pulse width-modulated drive of the solenoid valve or with a separate adjustment means.

The conveying pump 16 is always switched on given withdrawal of water at the equipment 1-3, i.e., for example, when the solenoid valve 21 is activated for filling the oral glass of the filling means 3. The analogous case applies to shut-off valves (not shown) that are present in the handpieces 1 and 2.

A centrifugal pump, or turbine or rotary pump, can be advantageously utilized as a suitable conveying pump that must make available a constant water pressure of approximately 2.2 bar with respect to the instruments 1 and 2, as well as a variable conveying quantity of approximately 1.5 liters/min. with reference to the instruments or to the filling means 3. It is especially advantageous, however, to provide a motor-driven positive-displacement pump, which is schematically shown in the circuit diagram of FIG. 2. A positive displacement pump 24 is driven by an electric motor 23. The electric motor is switched on and off by a monometric switch 25, which senses pressure changes in an accumulator 26 and will switch the motor 23 on if there is a pressure drop due to an opening of a discharge at one of the withdrawal locations and will switch the motor 23 off when there is a pressure rise due to the closing of a discharge at a withdrawal location.

Figure 3:
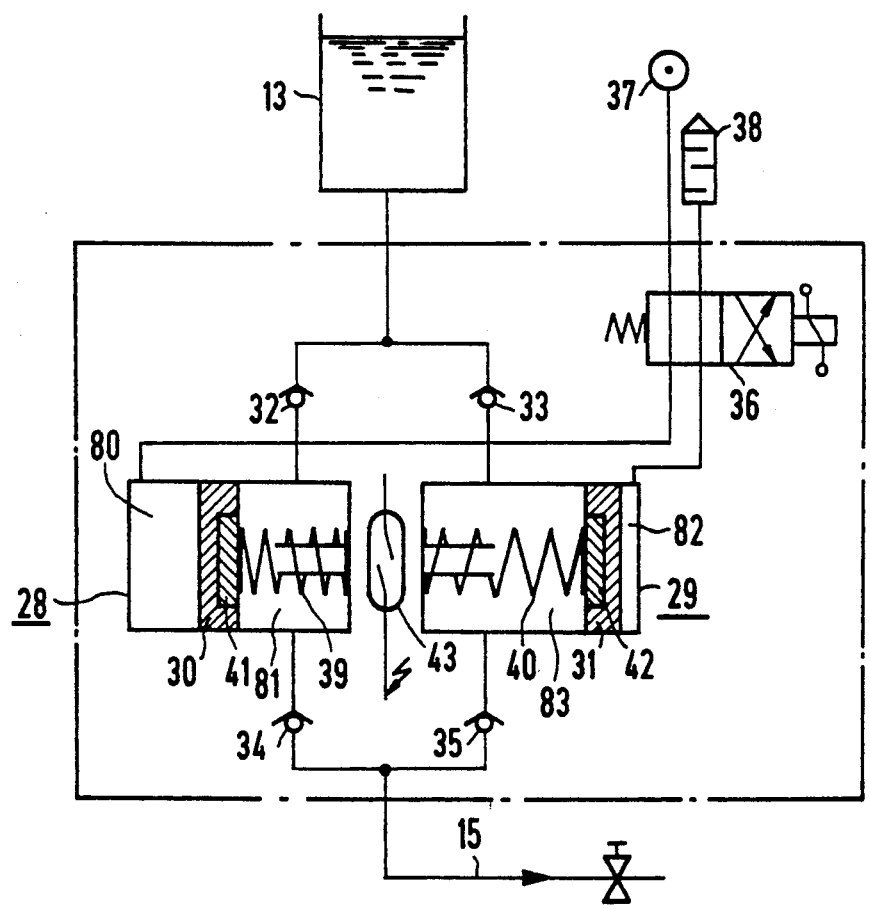
FIG. 3 is a hydraulic circuit diagram of a different embodiment of the air-driven hydraulic actuator.

FIG. 3 shows a hydraulic circuit diagram wherein two pneumatically chargeable and asynchronously operating reciprocating pumps 28 and 29 are provided as the air-driven hydraulic actuator. The cylinder for the pistons 30 of the pump 28 is divided by the piston into an air space or side 80 and a water side or space 81. In a similar way, the piston 31 divides the cylinder for the pump 29 into an air space or side 82 and a water side 83. The water side 81 is connected by lines including a check or clack valve 32 to the container 13 and also is connected by lines having a check valve 34 to the line 15. In a similar way, the water side 83 is connected through a check valve 33 to the container 13 and by a check valve 35 to the line 15. The air space 80 and 82 of the two pumps are connected by lines through a 4/2-way valve 36 to a compressed air generator 37 and to an exhaust muffler 38. Thus, as illustrated, the valve 36 in its illustrated position connects the compressed air generator 37 to the air side 80, while the air side 82 is connected to the exhaust air muffler 38. When the valve is switched to the second position, these connections are reversed. The pistons 30 and 31 are each biased by springs 39 and 40, respectively, into their respective air sides 80 and 82. The pistons 30 and 31 contain magnets 41 and 42 that cooperate with a reed contact 43. The 4/2-way valve 36 is switched with such a contact arrangement.

Figure 2:
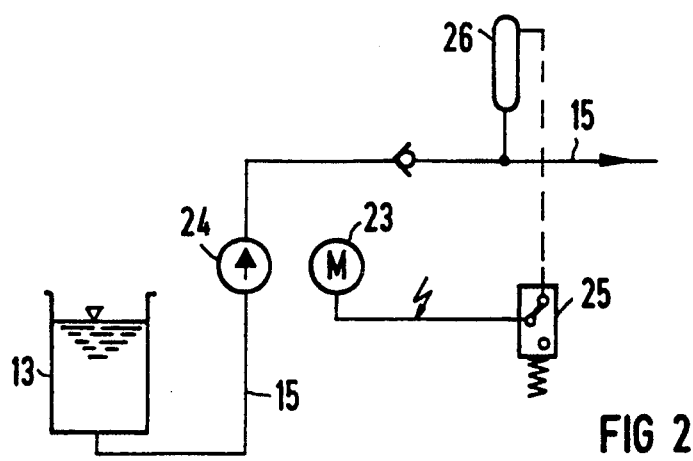
FIG. 2 is a hydraulic-electric circuit diagram for driving a first version of the air-driven actuator.

It should be mentioned for the function execution that the pump 16 of FIG. 1 or, respectively, the pump 24 of FIG. 2 begins to convey as soon as liquid is withdrawn from one of the user locations. Compressed air is conveyed into the air space 80 for the pump 28 from the compressed air generator 37. As a result, the air pressure building up in the air side 80 forces the piston 30 to move and to force the water situated in the hydraulic or water side 81 out through the line 15. As soon as the piston 30 has reached its ultimate position, it will trigger an electrical signal via the reed contact 43, with which the 4/2-way valve is switched. The other piston 31 of the pump 29 is now charged with compressed air at its air side 82 as the air side 80 is connected to the muffler 38. The compression spring 39 will see that the piston 30 is quickly returned to its initial position. While air is being expelled from the reciprocating pump 28 by the piston 30, the water side 81 simultaneously intakes fluid from the container 13.

Figure 5:
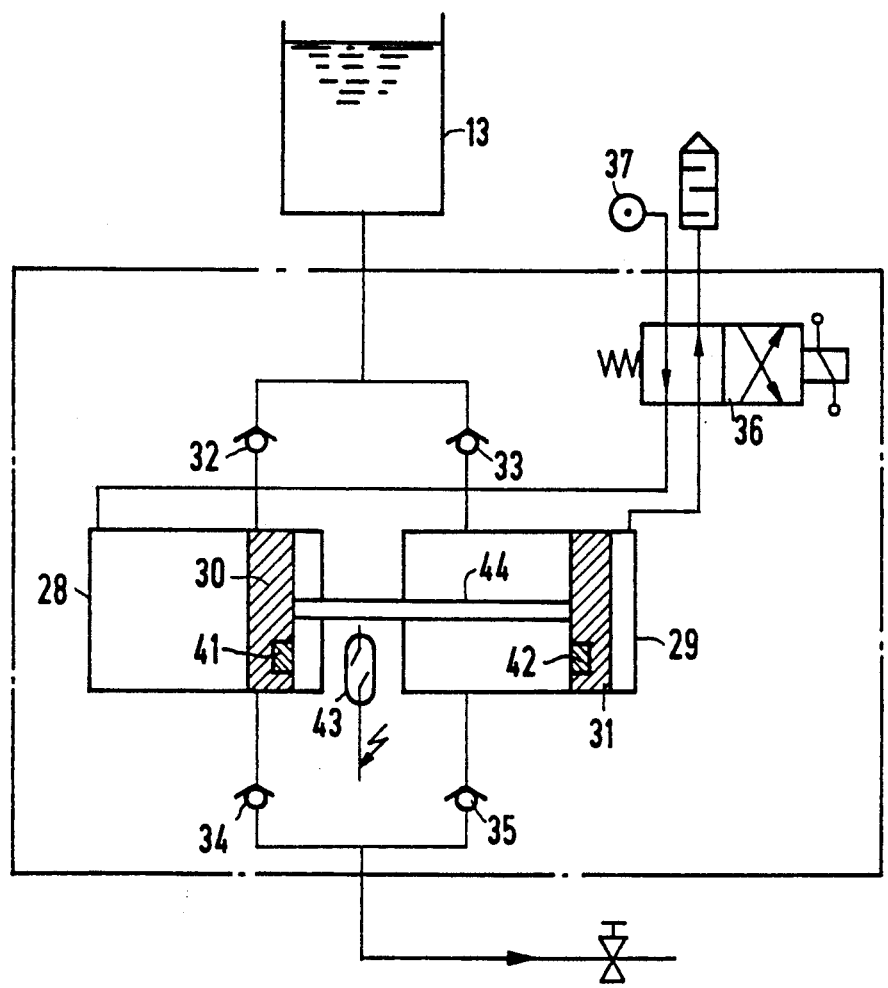
FIG. 5 is a circuit diagram of a modified air-driven actuator of FIG. 3.

A modification of the structure of the pump of FIG. 3 is illustrated in FIG. 5, and this modification has the two pistons rigidly connected to each other by a common piston rod 44. Thus, the compression springs can be eliminated. In this embodiment, while one piston of one pump is conveying liquid, it communicates a part of its energy supplied by the compressed air to the second piston of the second pump via the common piston rod 44 for causing an intake of the liquid into the second pump and for expelling the air from the second pump. In this version, too, the reversal of the two pistons in the two mutual positions occurs via the prescribed sensor mechanism.

It should be pointed out, of course, that two 3/2-way valves can also be provided instead of one 4/2-way valve.

Figure 4:
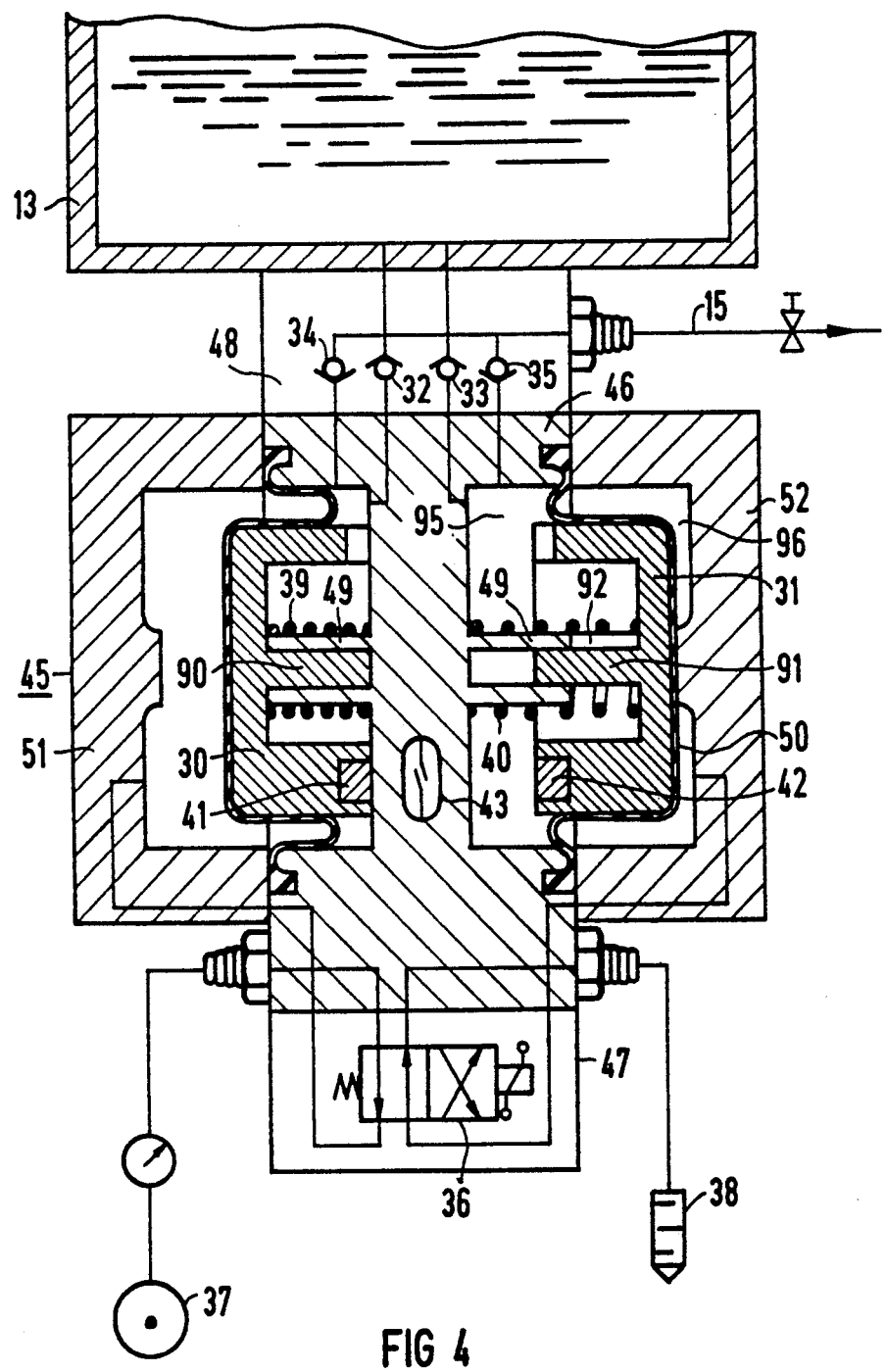
FIG. 4 is a cross sectional view of an air-driven actuator shown in FIG. 3.

FIG. 4 is a longitudinal cross sectional view of an actual structure of an arrangement that is schematically illustrated in FIG. 3. The structural unit referenced overall as 45 contains the two reciprocating pumps 28 and 29, the 4/2-way valve 36, as well as the four check valves 32-35. The structure includes an I-shaped-like carrier part 46 to which the valve blocks 47 and 48 are connected. The valve block 47 contains the 4/2-way valve 36, while the valve block 48 contains the check valves 32-35. The structure 46 has guide shoulders 49 for guiding pistons 30 and 31, which pistons have a pot-like shape. The guide shoulders 49 are fashioned so that the two pistons are guided and protected against turning and tilting. This can be accomplished by having the guide shoulders 49 receiving piston stems 90 and 91, respectively, and by providing the stem with a spline, such as 92 that is received in a keyway of the sleeve 49. As illustrated, the end stops are defined, first, by the housing covers 51 and 52, and also by the skirt of each of the pistons 30 and 31 engaging the carrier part 46. The separation between the hydraulic or water space, such as 95 for the piston 31, and the air space 96 is formed by a roll-type diaphragm 50 that is clamped between the carrier part 46 and the housing cover 52. A similar diaphragm is provided between the housing cover 51 and the carrier 46 for the piston 30.

The lines leading to and from the valves are worked into the two valve blocks 47 and 48, and in the carrier part 46 and into the two housing covers 51 and 52. Two magnetic lamina 41 and 42 are arranged as inserts in the pot-shaped pistons, and the protective contact or reed switch cooperating therewith is integrated in the carrier part 46 in a suitable way. The two compression springs, such as 39 and 40, are fashioned so that, due to the spring power exerted by them, the pistons intake liquid from the container 13 or, respectively, displace air from the pneumatic space, such as 96, at an adequate speed. The mixing vessel 13 is expediently put in place on the valve block 48 of the structural unit 45.

It should be noted regarding the control that the ultimate piston positions are acquired by the reed contact or switch 43. The steeply rising voltage edge, that is formed when the contact is closed, is employed as a switching signal for the solenoid valve 36. In order to avoid disruptions in the control, for example due to intersections of magnetic fields produced by the two magnets 41, 42, it is proposed that the solenoid valve be intentionally driven after a maximum closing time $t_{max}$ of the reed contact 43 that can be empirically defined. Switching errors can be compensated by such a force control.

Based on the fact that the stroke volume of the two reciprocating pumps are known and the momentary conveying volume of the two pumps can be defined with the switching frequency of the reed contact, the switching or reversing signals of the reed contact can be simultaneously, advantageously used as information signals and/or control signals for the presence of a flow, since the two reciprocal pumps only start up when liquid is being withdrawn. A further simplification of the means can be achieved on the basis of this multiple exploitation of the signals.

Although various minor modifications may be suggested by those versed in the art, it should be understood that we wish to embody within the scope of the patent granted hereon all such modifications as reasonably and properly come within the scope of our contribution to the art.

We claim:

1. In a water supply device for a dental work station containing a plurality of equipment comprising water exits and withdrawal locations and to which water is supplied from a feed water line of a drinking water line network, wherein at least one of the withdrawal locations cannot be arranged at a safe distance with respect to a drain allocated to the withdrawal location that is required according to technical rules for protecting drinking water from a backflow, the improvements comprising isolation means being provided in a line leading from the feed water line of the drinking water line network to at least said withdrawal locations, said isolation means separating the feed water line from said withdrawal location within the framework of the prescribed safety measurements; and pump means being provided in a line section following the isolation means, said pump means increasing the water pressure in said line section to a value required at each of the withdrawal locations.

2. In a water supply device according to claim 1, wherein the isolation means comprises a first container into which water from the feed water line is introduced via a free discharge.

3. In a water supply device according to claim 2, which includes a second container being provided with disinfectant, said second container discharging into the first container with a free discharge.

4. In a water supply device according to claim 3, which includes control means cooperating with the first container to insure delivery of disinfectant from the second container as water is added to the first container.

5. In a water supply device according to claim 1, wherein the pump means comprises a hydraulic pump controlled by a manometric switch that responds dependent on line pressure in the line section leading from said isolation means.

6. In a water supply device according to claim 5, wherein a hydraulic accumulator is connected to said line section and said manometric switch senses the pressure changes in said accumulator.

7. In a water supply device according to claim 5, wherein the pump means is a motor-driven positive displacement pump.

8. In a water supply device according to claim 1, wherein the pump means comprises two pneumatically chargeable hydraulic pumps that work asynchronously and convey water with constant pressure from the isolation means to the withdrawal location.

9. In a water supply device according to claim 8, wherein the two hydraulic pumps each have a pump housing having a piston guided therein for movement with means preventing twisting and tilting, each of said pump housings including means for causing the piston to move in a direction to displace air out of the housing.

10. In a water supply device according to claim 9, wherein the pistons are fashioned pot-shaped and have a roll-type diaphragm clamped in the pump housing to provide a partition between a hydraulic space and an air space.

11. In a water supply device according to claim 10, wherein the means for causing the piston to discharge air from the air space includes a compression spring biasing the piston in a direction to expel air from the air space.

12. In a water supply device according to claim 9, wherein the means for causing the piston to move to expel air includes a common piston rod interconnecting the two pistons so that while one piston is being moved by compressed air, the other piston is being moved to discharge air from the air space.

13. In a water supply device according to claim 9, which includes solenoid valve means for controlling the flow of compressed air to each of the pumps, sensor means for determining the ultimate position of the piston in each of said pumps including a magnetically actuated reed contact means.

14. In a water supply device according to claim 13, wherein the reed contact means includes permanent magnets built into each of the pistons.

15. In a water supply device according to claim 14, wherein the reed contact means has contact paddles which are moved into a closed position by one of the magnets, and wherein a voltage peak created by the contact paddles being closed is utilized as a switching signal for the solenoid valve.

16. In a water supply device according to claim 15, wherein the solenoid valve includes means for forcibly driving the valve after a chronologically defined closing time $t_{max}$ of the reed contact means for compensating for faulty switching.

17. In a water supply device according to claim 1, wherein the isolation means includes a first container receiving water from the feed water line via a free discharge, said first container having means for sensing the level of the fluid in said container, said device including a second container for a disinfectant having a free discharge with control means for discharging into said first container, said control means including a pulse width modulated-driven solenoid valves receiving inputs from said means for sensing.

18. In a water supply device according to claim 1, wherein the isolation means comprises a first container into which water from the feed water line is introduced via a free discharge, said pump means having an inlet connected to said container.

* * * * *